United States Patent
Donovan et al.

(10) Patent No.: US 6,810,286 B2
(45) Date of Patent: Oct. 26, 2004

(54) STIMULATION FOR DELIVERY OF MOLECULAR THERAPY

(75) Inventors: Maura G. Donovan, St. Paul, MN (US); Orhan Soykan, Houghton, MI (US); D. Curtis Deno, Andover, MN (US); Lawrence J. Mulligan, Andover, MN (US); Brian C. A. Fernandes, Roseville, MN (US)

(73) Assignee: Medtronic, Inc, Minneapolis, MN (US)

(*) Notice: Subject to any disclaimer, the term of this patent is extended or adjusted under 35 U.S.C. 154(b) by 0 days.

(21) Appl. No.: 09/799,304

(22) Filed: Mar. 5, 2001

(65) Prior Publication Data

US 2002/0010492 A1 Jan. 24, 2002

Related U.S. Application Data

(60) Provisional application No. 60/187,280, filed on Mar. 6, 2000.

(51) Int. Cl.⁷ .................................................. A61N 1/00
(52) U.S. Cl. ................ 607/2; 607/9; 607/11; 607/72
(58) Field of Search ................ 607/2, 4–5, 7, 607/9, 11, 39–58, 72, 3, 50

(56) References Cited

U.S. PATENT DOCUMENTS

| | | | |
|---|---|---|---|
| 3,543,762 A | 12/1970 | Kendall | 128/422 |
| 5,083,564 A | 1/1992 | Scherlag | 128/419 |
| 5,087,243 A | 2/1992 | Avitall | 604/20 |
| 5,186,181 A | 2/1993 | Franconi et al. | 128/804 |
| 5,433,735 A | 7/1995 | Zanakis et al. | 607/50 |
| 5,634,899 A | 6/1997 | Shapland et al. | 604/51 |
| 5,634,939 A | 6/1997 | Kuster et al. | 607/59 |
| 5,855,570 A | 1/1999 | Scherson et al. | 604/304 |
| 6,099,832 A | 8/2000 | Mickle et al. | 424/93.21 |
| 6,236,887 B1 * | 5/2001 | Ben-Haim et al. | 607/3 |
| 6,304,777 B1 * | 10/2001 | Ben-Haim et al. | 607/2 |
| 6,317,631 B1 * | 11/2001 | Ben-Haim et al. | 607/9 |

FOREIGN PATENT DOCUMENTS

| | | | |
|---|---|---|---|
| EP | 0 538 510 | 4/1993 | A61N/1/34 |
| GB | 1 394 171 | 5/1975 | G01N/27/50 |
| WO | WO 9302743 | 2/1993 | A61N/1/36 |
| WO | WO 9815317 | 4/1998 | A61N/1/05 |
| WO | WO 9857701 | 12/1998 | A61N/1/36 |
| WO | WO 9903533 | 1/1999 | A61N/1/362 |
| WO | WO00/27466 | 5/2000 | A61N/1/00 |
| WO | WO 00/27466 | 5/2000 | A61N/1/00 |

OTHER PUBLICATIONS

Hauck, US2002/0022863–A1, "Therapeutic Device and Method for Trreating Diseases of Cardiac Muscle", Feb. 21, 2002.*

Hauck, US2001/0031986–A1, "Therapeutic Device and Method for Treating Diseases of Cardiac Muscle", Oct. 18, 2001.*

Kanno, Shinichi, M.D. et al., Circulation, 1999; 99 pp. 2682–2687.

Kanno, Shinichi, M.D. et al., Circulation, 1999; 99 pp. 2682–2687.

* cited by examiner

*Primary Examiner*—Carl H. Layno
(74) *Attorney, Agent, or Firm*—Kenneth Collier; Girma Wolde-Michael

(57) ABSTRACT

Provided are novel stimulatory device for the controlled production of angiogenic growth factors. More specifically, a subthreshold pulse generator is used for the local production of vascular endothelial growth factor.

67 Claims, 8 Drawing Sheets

STIMULATION FOR DELIVERY OF MOLECULAR THERAPY

This application claims benefit of 60/187,280 filed Mar. 6, 2000.

FIELD OF THE INVENTION

The present invention provides a novel stimulatory device for the controlled production of angiogenic growth factors. More specifically, the present invention provides a subthreshold pulse generator for the local production of vascular endothelial growth factor.

BACKGROUND OF THE INVENTION

Coronary artery disease (CAD) results from arteriosclerosis of blood vessels serving the heart. Arteriosclerosis is a hardening and narrowing of the arteries. Often the arteries of the heart can suddenly become so severely blocked that there is inadequate blood supply to areas of the heart, leading to the occurrence of a myocardial infarction. The area of damage where the reduced blood flow has occurred is called the ischemic area. The ischemic area of the heart, because it does not get adequate blood flow, is starved of oxygen and nutrients. This blockage, if not treated quickly, can lead to severe tissue damage. Often surgical procedures are used to graft new blood vessels to the ischemic area to improve circulation. Alternatively, angioplasty or stenting of the blocked blood vessel is done to reopen or maintain blood flow. However, by-passing or reopening of the arteries is often not possible because of limitations of present methodologies and the risk to the patient from surgical intervention.

Damage from ischemia from insufficient blood circulation can also occur in blood vessels peripheral to the heart. Peripheral arterial occlusive disease (PAOD), caused by arteriosclerosis or by formation of vascular blood clots from diseases such as diabetes, often leads to loss of external limbs.

One way to address the need for improved blood flow to ischemic tissue is to generate new blood vessels. Angiogenic factors are known to directly participate in the formation of new blood vessels. Local administration of recombinant angiogenic growth factors, such as basic fibroblast growth factor (bFGF) and vascular endothelial growth factor (VEGF), can salvage ischemic areas of myocardial and skeletal muscle tissue in animal models. A number of approaches have been developed to deliver these factors to ischemic areas in hope of developing new blood vessels, including direct injection, electroporation, and delivery using retroviral vectors.

The direct injection of angiogenic growth factors has many problems associated with it, most notably problems with effective delivery of the factors into the cells. Electroporation is a possible method of delivery of genetic materials encoding angiogenic factors; however, the transfection efficiency is still very low and the high-energy pulses directed to the tissue often kill many healthy cells. Alternatively, others have sought to develop viral based gene delivery systems to directly produce angiogenic factors in vivo; however, this approach requires considerably more development before it is considered to be a safe and effective therapy. Although extensive research continues in the areas of gene delivery, very little has been reported on methods to control and regulate gene expression in vivo. The inability to effectively deliver the agent to the target tissue, therefore, is one of the major limitations of the use of such agents. During delivery of the angiogenic factors the effectiveness is often destroyed or lost.

Recent work has been published related to using electrical fields to stimulate natural production of angiogenic growth factors. WO 00/27466 describes use of constant voltage sources to generate electrical fields for stimulating angiogenesis. The described voltages are on the order of 50–300 volts/cm, which would also stimulate contractile responses during stimulation. Stimulation of angiogenesis without causing a contractile muscle response would be advantageous. In a recent publication (Circulation, 1999;99:2682–2687) it was reported that low-voltage electrical stimulation of skeletal muscle induced de novo synthesis of VEGF protein and promoted angiogenesis. Further work is needed in this research area. Even with the known methods in the art, there still exists a need for additional and more effective subthreshold devices and more efficient methods for the controlled delivery of angiogenic growth factors to promote angiogenesis in muscle tissue, and methodologies that can be used to stimulate angiogenesis in cardiac and vascular tissue.

SUMMARY OF THE INVENTION

The present invention addresses a number of problems existing in the prior art with respect to controlled local delivery of angiogenic factors. Various embodiments of the present invention provide solutions and to one or more of the problems existing in the prior art with respect to delivery of angiogenic factors. The present invention provides a novel electrical pulse generator for angiogenesis and production angiogenic growth factors.

The present invention provides an electrical pulse generator for providing subthreshold pulses. The present device can be adapted to a range of subthreshold pulses by modulating the time, frequency, and delivery of a given stimulus. The present generator allows the use of a constant voltage, regardless of the distance between electrodes by allowing a variable field density. The present generator allows for control over the amplitude of the voltage and for charge balancing of the delivered and recovered charged pulse.

In another embodiment, the subthreshold pulse generator can be used externally, but preferably is designed and configured to be implantable. The subthreshold pulse generator includes a power supply and a control mechanism interconnected with the power supply. Optionally, the pulse generator can be used with a plurality of electrodes in electrical communication with the power supply. The present generator is also capable of checking the lead continuity at a predesignated time.

The invention also provides a subthreshold pulse generator for a patient in need thereof. In one aspect, the invention includes a method for reducing or repairing tissue injury or disease by providing a means for regulating angiogenic growth factor production. In another aspect the subthreshold stimulation provided is sufficient to stimulate angiogenesis in the targeted body tissue. In yet another aspect, the present invention provides a novel method of pacing that is capable of stimulating cells or tissues for the controlled expression of angiogenic factors.

These and other objects and features of the invention will become more fully apparent when the following detailed description is read in conjunction with the accompanying drawings.

BRIEF DESCRIPTION OF THE DRAWINGS

The following drawings depict certain embodiments of the invention. They are illustrative only and do not limit the invention as otherwise disclosed herein.

FIG. 1 is an overview of one mode of operation for subthreshold stimulation of cardiac tissue.

FIG. 2 illustrates the schematic of the output circuitry of a subthreshold stimulation device for a pulse generator.

FIG. 3 illustrates the schematic of the output circuitry of a subthreshold device for a pulse generator during the output stage.

FIG. 4 illustrate a pacing scheme for providing a series of subthreshold stimulations.

FIG. 5 shows a block diagram of a circuit for pulse generator capable of delivering electrical stimulation to the target tissue cells.

FIG. 6 illustrates the schematic of the output circuitry of a subthreshold stimulation device for a subthreshold pulse generator.

FIG. 7 shows a western blot of VEGF protein in stimulated and unstimulated vascular tissue.

DETAILED DESCRIPTION OF THE INVENTION

Definitions

Figure 1:
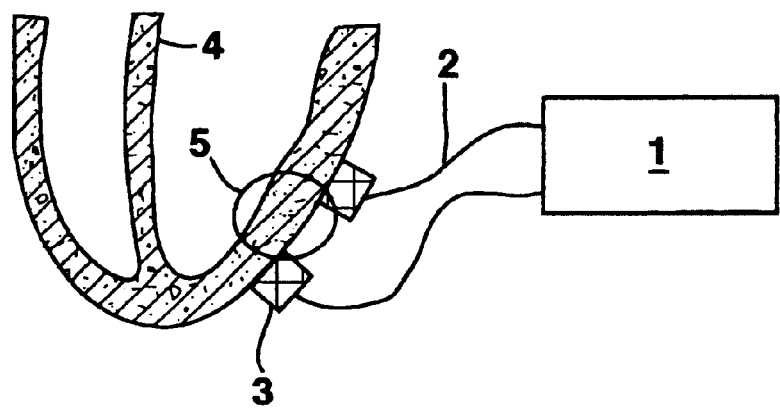
FIG. 1: Subthreshold Stimulation of Heart Tissues For Production of VEGF.

"Angiogenic factors" are a group of substances that promote angiogenesis in a tissue. These factors include, but are not limited to, vascular endothelial growth factor (VEGF) and fibroblast growth factor (FGF) and all natural analogs found encoded in the genome of the patient that are structurally and/or functionally related members of these factors.

The term "mature protein" or "mature polypeptide" as used herein refers to the form(s) of the protein produced by expression in a mammalian cell. It is generally hypothesized that, once export of a growing protein chain across the rough endoplasmic reticulum has been initiated, proteins secreted by mammalian cells have a signal sequence which is cleaved from the complete polypeptide to produce a "mature" form of the protein. Often, cleavage of a secreted protein is not uniform and may result in more than one species of mature protein. The cleavage site of a secreted protein is determined by the primary amino acid sequence of the complete protein and generally cannot be predicted with complete accuracy. However, cleavage sites for a secreted protein may be determined experimentally by amino-terminal sequencing of the one or more species of mature proteins found within a purified preparation of the protein.

"Operably coupled" refers to the transference of an electrical stimulus by a subthreshold pulse generator to a tissue. A subthreshold pulse generator operably coupled with tissue or cells refers to a configuration where an electrical stimulus is delivered to the tissue or cells to cause an increase in available angiogenic factors. Usually the stimulus is delivered from the subthreshold pulse generator through leads to electrodes attached to the tissue The terms "treating", "treatment", and "therapy" as used herein refer to curative therapy, prophylactic therapy, and preventive therapy. An example of "preventive therapy" is the prevention or lessening of a targeted disease or related condition thereto. For example, subthreshold stimulation can be used prophylactically to promote angiogenesis as a preventive effort to avoid the occurrence of a myocardial infarction. Those in need of treatment include those already with the disease or condition as well as those prone to having the disease or condition to be prevented. The terms "treating", "treatment", and "therapy" as used herein also describe the management and care of a patient for the purpose of combating a disease or related condition, and includes the administration of at least one subthreshold electrical pulse to an ischemic area to improve blood flow to the tissue.

"Chronic" administration refers to administration of an electrical stimulus in a continuous mode as opposed to an acute mode, so as to maintain the initial therapeutic effect (activity) for an extended period of time.

"Intermittent" administration is treatment that is not consecutively done without interruption and is repeated in the course of time.

"Ischemia" is defined as an insufficient supply of blood to a specific organ or tissue. A consequence of decreased blood supply is an inadequate supply of oxygen and/or nutrients to the organ or tissue. Prolonged ischemia may result in injury to the affected organ or tissue. "Anoxia" refers to a virtually complete absence of oxygen in the organ or tissue, which, if prolonged, may result in death of the organ or tissue.

"Ischemic injury" refers to cellular and/or molecular damage to an organ or tissue as a result of a period of ischemia and/or ischemia followed by reperfusion.

"Hypoxic condition" is defined as a condition under which a particular organ or tissue receives an inadequate supply of oxygen.

"Anoxic condition" refers to a condition under which the supply of oxygen to a particular organ or tissue is cut off.

"Reperfusion" refers to the resumption of blood flow in a tissue following a period of ischemia.

The term "patient" as used herein refers to any mammal, including humans, domestic and farm animals, and zoo, sports, or pet animals, such as cattle (e.g., cows), horses, dogs, sheep, pigs, rabbits, goats, cats, and non-domesticated animals such as mice and rats. In a preferred embodiment of the invention, the mammal is a human, dog, rabbit, or mouse.

A "therapeutically effective amount" as referred to herein is the minimal amount of subthreshold stimulation that is necessary to impart a therapeutic benefit or a desired biological effect to a patient. For example, a "therapeutically effective amount" for a patient suffering from ischemia is such an amount which induces, ameliorates, or otherwise causes an improvement in the amount of angiogenic factors available or otherwise improve circulation in the tissue. For example, a "therapeutically effective stimulus" is the amount of electrical stimulation necessary to express a therapeutically effective amount of an angiogenic protein in an amount to provide a therapeutic benefit or provides at least one measurable improvement in circulation.

The term "pace" as used herein is the act of issuing an electrical subthreshold stimulus delivered to the cellular tissue delivered a subthreshold pulse generator. "Pacing" generally refers to the act of repeatedly issuing an electrical stimulation to the tissue, as in the present case, delivering a series of subthreshold stimulations to the tissue.

"Pharmacologically effective stimulus" is the amount of stimulus needed to provide a desired level of an angiogenic protein in the patient. The precise amount of stimulation or pacing needed will depend upon numerous factors, e.g., such as the specific angiogenic factor involved, the delivery stimulus employed, characteristics of stimulus provided, its intended use, and patient considerations. These determinations can readily be determined by one skilled in the art in view of the information provided herein.

The term "administer an electrical stimulus" means to deliver electrical stimulation to a tissue. As applied in the present invention, the electrical stimulus is delivered to the tissue by a subthreshold pulse generator.

"Threshold" versus "subthreshold" stimulation refers to a relative level of applied stimulation. "Threshold" stimulation as used herein, refers to a level of stimulation to evoke a gross tissue electrical or mechanical response in the excited tissue, e.g. the minimum electrical stimulus needed to consistently elicit a cardiac depolarization for a heart contraction or to elicit a skeletal muscle movement. Generally, threshold stimulation is greater than 1.0 volt. Subthreshold stimulation refers to the application of electrical stimulation to tissue at levels low enough not to elicit a gross electrical or mechanical response from the tissue, such as to not cause cardiac depolarization or muscle contraction. A subthreshold stimulus can be achieved by keeping either the voltage amplitude and/or the duration of the electrical pulses below the threshold response levels for gross motor or nerve responses. Generally, subthreshold stimulus is less than or equal to 1.0 volt. Subthreshold stimulation allows one to deliver electrical stimulation to the tissue to increase the levels of angiogenic protein available without having the unwanted side effects due to the stimulation of nerve or muscle cells, such as unwanted contraction and or uncomfortable tactile sensations, and the like.

As used herein, a number of terms for measured physical parameters have been abbreviated: amplitude may be expressed in volts (V) or millivolts (mV); current may be expressed in amperes (amps) or milliamperes (mamps); and pulse width, frequency, or timing in milliseconds (msec); and energy in joules (J) or millijoules (mJ).

Description

In general the present invention relates to a subthreshold pulse generator for producing an electrical field near to or within a targeted body tissue and methods of treating damaged or ischemic tissue by stimulating angiogenesis. In one embodiment the electrical field is delivered directly to the target area located between a plurality of electrodes. As an example, FIG. 1 (FIG. 1) illustrates a subthreshold pulse generator (1) creating a subthreshold electrical field (5) to the lower ventricle of the heart (4) through a pair of leads (2) and electrodes (3).

Subthreshold stimulation has been demonstrated to promote production of angiogenic growth factors. The promotion of angiogenic response by the present device thereby serves as a significant adjunct over current surgical methods of intervention to re-establish circulation to ischemic tissue areas.

Purpose of the Subthreshold Pulse

The present invention provides a novel subthreshold electrical pulse generator (also referred to herein as subthreshold pulse generator, pulse generator, or generator). The pulse generator has the essential feature of being capable of providing an electrical stimulus or series of electrical subthreshold stimulations or pulses (pacing). The subthreshold electrical stimulus or pulses are used to induce angiogenesis in targeted cells or tissues. In one embodiment, the electrical stimulator provides a subthreshold stimulation to activate transcription of at least one angiogenic factor. The objective of the subthreshold stimulation is not to excite the tissue for mechanical contraction but to selectively activate angiogenesis.

It is envisioned that different stimulation therapies may be given in conjunction with a course of subthreshold stimulation therapy. At times, particularly when considered with benefits of threshold electrical stimulation of traditional pacemakers, it may be advantageous to combine the features of a traditional pacemaker with components for subthreshold stimulation.

Pulse Generator Operation Parameters

The controlled output voltage from the subthreshold electrical pulse generator can be adjusted for a wide range of tissue impedances, such as from 35 Ω to infinity. Through a variety of unique combinations of voltage and timing settings the present device provides a unique mechanism to increase production of angiogenic factors while not evoking contractile responses The present generator allows the use of a constant voltage, regardless of the distance between electrodes, by allowing a variable field density. The present generator allows for control over the amplitude of the voltage and for charge balancing of the delivered and recovered charged pulse. As a specific embodiment, the subthreshold pulse generator allows the use of a constant voltage by allowing a variable field density of about 30% of the targeted voltage, more preferably of about 20% of the targeted voltage, and even more preferably of about 10%, and most preferably of about 5% of the targeted voltage. As will be illustrated later, the subthreshold voltage is at a constant level, allowing the field intensity to vary across the tissue. Effective results were obtained in the in vitro experiments having a variable field intensity in vitro (see Experiment 1, Table 1) as well as with stimulating VEGF production in vivo (see Experiment 2, FIG. 7).

In one embodiment, the subthreshold pulse generator is capable of delivering an electric field to the targeted body tissue of 0 to 1.5 V output in steps of 0.1 V, wherein the electric field is generally less than or equal to about 1 V/cm, and more preferably less than about 0.5 V/cm, and even more preferably about 0.1 V/cm. I In yet another embodiment, the subthreshold field can be produced by a number of pulses with a frequency about 10 Hz to about 100 Hz, and preferably with a frequency of about 25 Hz to about 85 Hz, and more preferably with a frequency of about 40 Hz to about 70 Hz, and even more preferably with a frequency of about 50 Hz to about 60 Hz, and most preferably with a frequency of about 50 Hz.

In a further embodiment, the stimulation period is less than the pulse cycle (1/frequency). The stimulation period can be chosen to be between about 100 msec and 0.01 msec, between about 50 msec and 0.05 msec, and between 3 msec and 0.1 msec, wherein the actual value can be less than about 20 msec, preferably less than about 10 msec, more preferably less than about 3 msec or any value between 0.1 ms and 3.0 ms.

Subthreshold Stimulation

Figure 2:
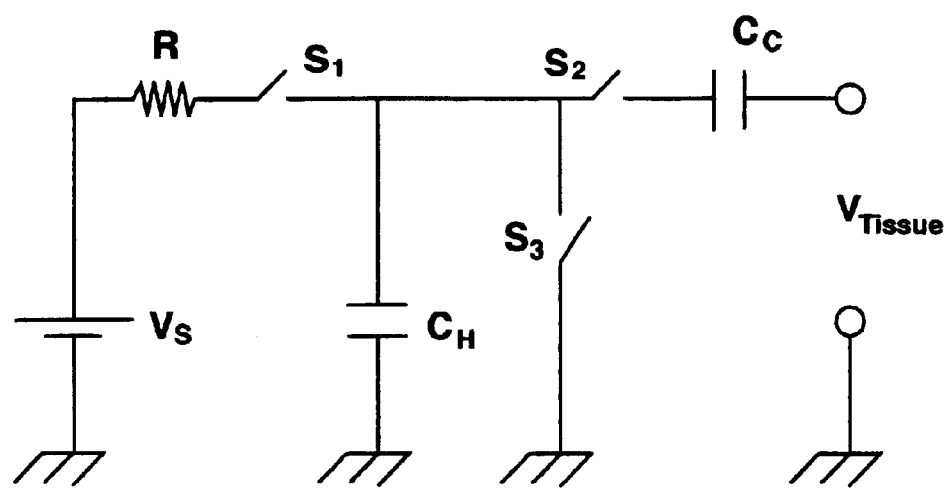
FIG. 2: Simplified Schematic of The Output Circuit for Subthreshold Stimulation
Figure 3:
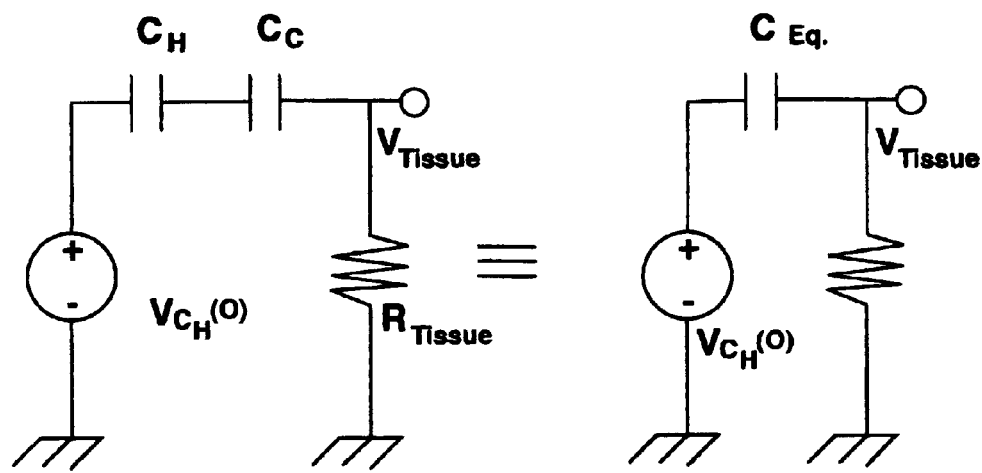
FIG. 3: Equivalent Circuit of the Subthreshold Stimulation During the Output Stage
Figure 4:
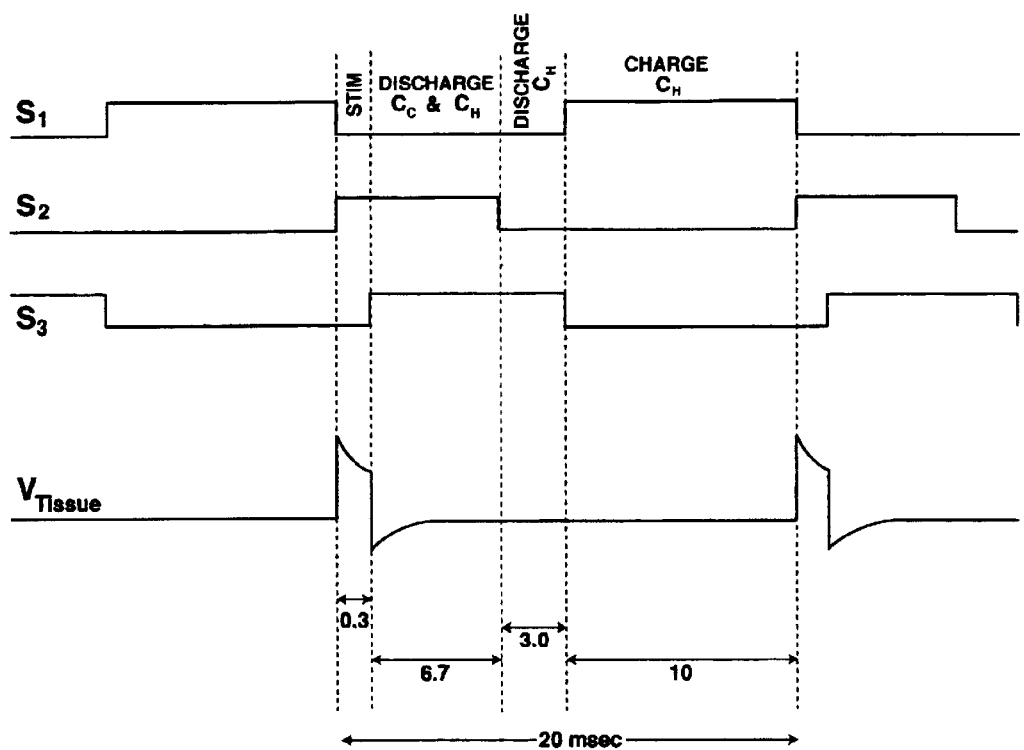
FIG. 4: Subthreshold Stimulation Sequence

The schematic of the output circuitry in FIG. 2 is a simplified illustration of the schematic of the operating circuitry for a subthreshold pulse generator. FIG. 2 is useful for setting basic design requirements of a subthreshold pulse generator: $S_1$, $S_2$, and $S_3$ are switches that are opened and closed during the operating cycle, R is a circuit resistor, Vs is the battery, and $C_H$ and $C_C$ are capacitors. For example, if the component values can be chosen as follows: VS=2.8 Volts, R=25 Ω, $C_C$=$C_H$=10 µF, one can calculate that $C_H$ will have 0.110 volts at the end of 10 msec charging phase as shown in FIG. 4. By this illustration, one skilled in the art could choose a number of settings that would provide $C_H$ at any given set of subthreshold output voltages. FIG. 3 shows the equivalent circuit of the output stage during the stimulation phase. $V_C$ represents the initial condition on the $C_H$. In this case, because $C_H$, $C_C$ and $R_{tissue}$ are connected in series, one can combine $C_H$ and $C_C$ into $C_{eq}$=5 µF. Voltages seen at the electrodes are given by: $V_{Tissue}(t)=V_{CH}(0)\{1-\exp[-t/(C_{Eq}R_{Tissue})]\}$. If, for example, the output voltage is allowed to change by only 10%, then the $V_{Tissue}(t)$ will vary between 0.110 volts and 0.090 volts. That would indicate that $V_{CH}(0)$=0.110, and $V_{Tissue}(t)$ (0.3 msec)=0.090. Rewriting the equation for the tissue voltage, 0.090=0.110 $\{1-\exp[-t/(C_{Eq}R_{Tissue})]\}$, t=0.3 msec or 0.090=0.110 $\{1-\exp[-0.3\times10^{-3}/(5\times10^{-6}\times R_{Tissue})]\}$ and solving for $R_{Tissue}$ one can find that $R_{Tissue}$=35 Ω. In other words, the minimum tissue impedance that one can drive will be 35 Ω, with output voltage staying in the 90–110 mV range. Use of the above settings in the pulse generator provides one example for (1) a pulse generator for subthreshold stimulation; (2) controlled output voltage for a wide range of tissue impedances (35 Ω to infinity); (3) a pacing output for subthreshold stimulation where the objective is not to excite the tissue for mechanical contraction but to increase the amounts of angiogenic factors available by providing a set of variables equal to or less than a 1.0 volt subthreshold stimulus.

FIG. 4 (FIG. 4) exemplifies a set of subthreshold stimulation parameters. FIG. 4, illustrates the timing diagram of the electrical pulses and charging of capacitors, to provide the illustrated pulse train: pulse frequency of 50 Hz (20 msec); stimulatory pulse of 0.3 msec to the tissue (Vtissue) and a 6.7 msec discharge (recharge with opposite polarity for charge balance). The remaining 13 msec of the pulse cycle electrodes are floating, and capacitors are recharged.

Figure 5:
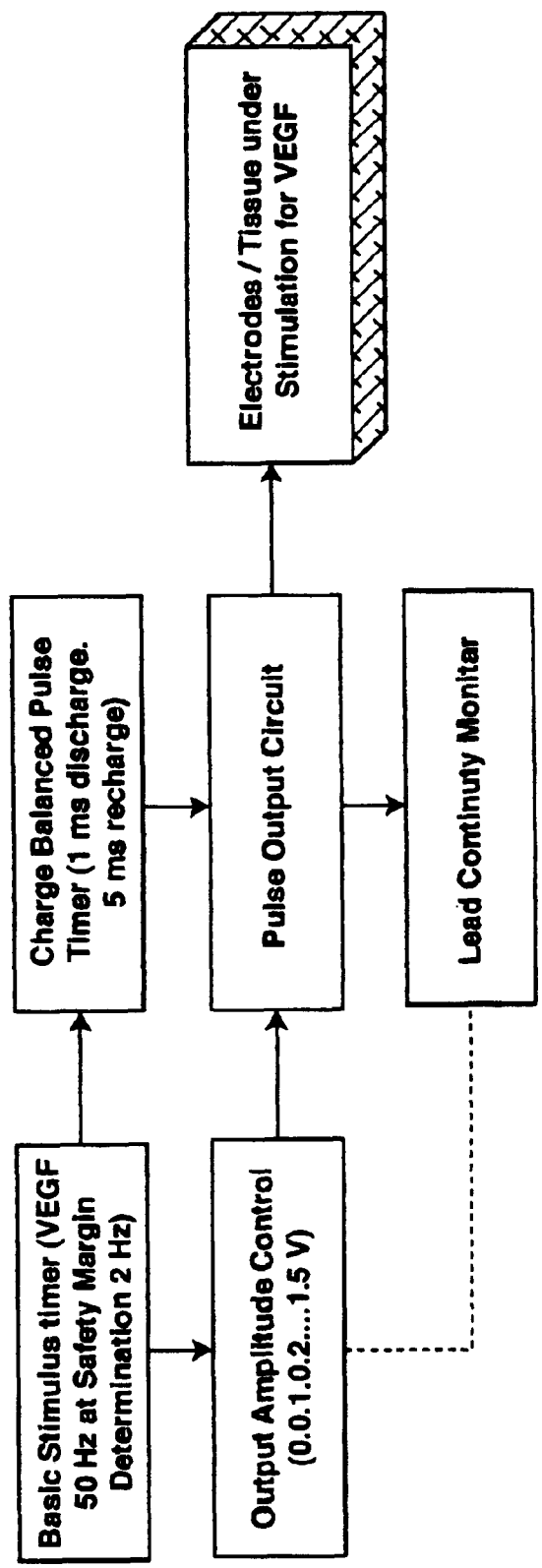
FIG. 5: Pulse Generator for Subthreshold Stimulation

FIG. 5. (FIG. 5) is a block diagram of a subthreshold stimulator employed in chronic animal studies. The basic stimulus repetition frequency of 50 Hz is generated by the clock/timer at upper left. This triggers timers that control the 1 msec discharge and 5 msec recharge phases of each output pulse (top center). Pulse amplitude is controlled by 4-bit DAC (left center). The pulse output circuit (center) utilizes the timing and amplitude information to generate the actual output pulse which is, in turn, delivered to electrodes and the tissue (right center). The pulse output circuit (bottom center) optionally incorporates a lead continuity monitor to check for lead or electrode malfunction. Output amplitude may be adjusted (dashed line) based on conditions of increased electrode resistance, or turned off if a lead breaks or shorts. An alternative stimulation setting of 2 Hz (upper left) is employed for evaluation of the stimulation safety margin (pacing threshold) in conjunction with the output amplitude control.

FIG. 6 (FIG. 6) shows the stimulator circuit used during in vivo experiments. Explanations of general symbols used in the circuit diagram are as follows:

U: Integrated Circuit
R: Resistor
C: Capacitor
SW: Switch
D: Diode
Vcc: Positive terminal of the power supply (battery)
Vee: Negative terminal of the power supply (battery)
JP: Jumper terminal for off-board connections
Below is a list of components labeled specifically:
(1) U2: Main oscillator keeping the stimulator timing at 50 Hz (20 milli-seconds)
(2) U1B: Timer to control the stim pulse width, which closes S2 shown as (13).
(3) U1A: Timer to control the discharge duration, which closes S3, shown as (7).
(4) C11 is the holding capacitor, $C_H$, with the value of 10 micro-Farads.
(5) C10 is the coupling capacitor, $C_C$, with the value of 6.8 micro-Farads.
(6) JP2 is the header where the stimulation electrodes are attached.
(7) U5: Switch S3, when closed discharges the coupling capacitor.
(8) R9: Resistor in series with the tissue being stimulated that is used to measure the stimulation current intensity.
(9) SW2: Switch to test lead integrity using the lead integrity indicator shown as (10)
(10) LED: Light emitting diode used as lead integrity indicator
(11) U7C: Digital to analog converter which is used to set the stimulation amplitude, Vadj, shown as (14).
(12) U7D: Inverter/driver for the adjustable stimulation amplitude determined by (11).
(13) U3: Switch S3, when closed, delivers charge from the holding capacitor to the tissue connected to (6).
(14) Vadj: adjustable stimulation amplitude determined by (11)

Figure 6A:
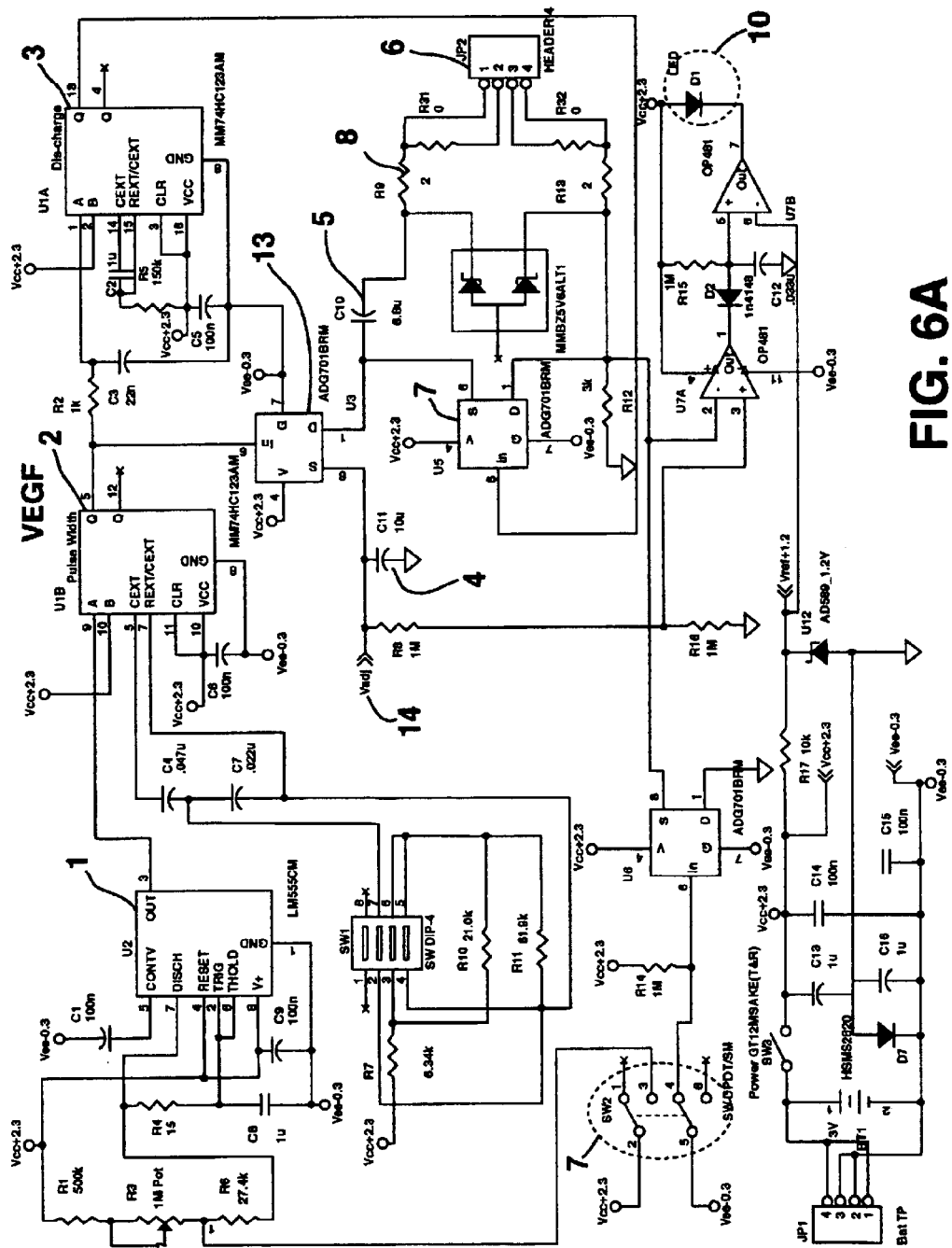
FIG. 6: Schematic of The Output Circuit for Subthreshold Stimulation
Figure 6B:
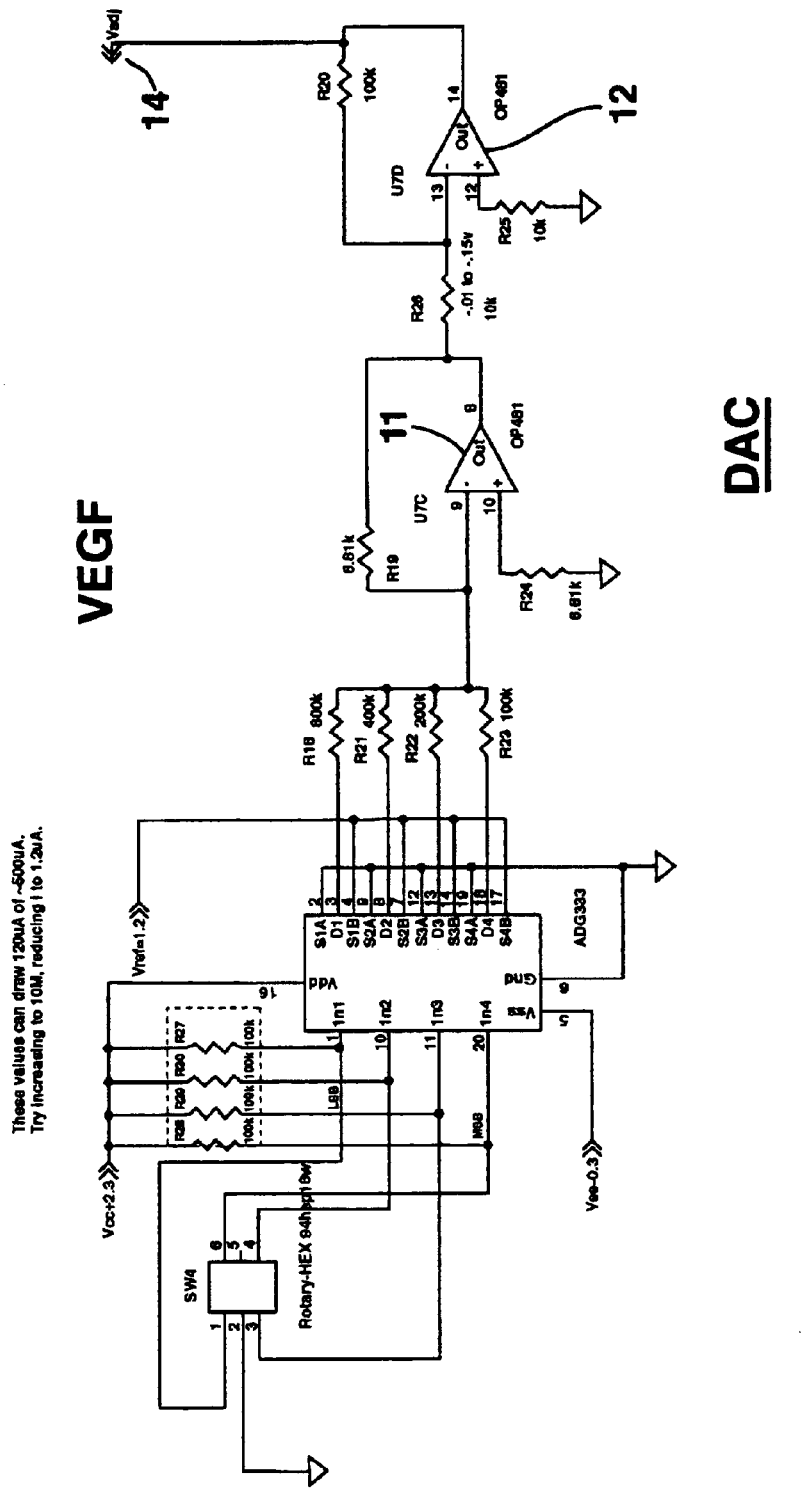

The subthreshold stimulator circuit of FIG. 6A (FIG. 6A) and continued on FIG. 6B (FIG. 6B) operates essentially to produce the stimulation waveform shown in FIG. 2. The generated stimulus is a periodic signal which main oscillator (1) is set to produce 50 Hz digital pulses, and provides the main clock. Timers (2) and (3) produce the stimulation and discharge pulses, respectively, from the clock, again as shown on FIG. 2. These pulses are used to close the switches (13) and (7), which correspond to $S_2$ and $S_3$ on FIG. 2. Terminals 1 and 4 of the on board connector (6) is where the leads going to the tissue are attached. During the stimulation, energy stored on holding capacitor (6) passes through switch (13), the coupling capacitor (5), and series resistor (8) to reach terminal (6) before arriving at the tissue. Voltage drop on series resistor (8) can be monitored from terminal (6) to get an indication of the current being passed through the tissue. Switch (9) can be used to monitor the lead integrity using the lead integrity indicator (10). Stimulation amplitude adjuster (14) is set by the digital to analog converter (11) followed by the inverter/driver (12).

Additional Features of the Subthreshold Pulse Generator

In another embodiment, the subthreshold pulse generator can be used externally, but preferably is designed and configured to be implantable. The present device can be implanted into the body and the electrical components sealed from the body tissues and fluids. Ideally, the implantable device has a volume of about 50 cm$^3$, preferably about 40 cm$^3$, more preferably about 30 cm$^3$, even more preferably about 20 cm$^3$, and most preferably about 10 cm$^3$.

It is envisioned that the electrical pulse generator can be implanted or can be external to the body. Ideally, the subthreshold pulse generator is implanted.

Electrodes and Leads

The subthreshold pulse generator includes a power supply and a control mechanism interconnected with the power supply. Optionally, the pulse generator can be used with electrodes in electrical communication with the power supply. In another embodiment he subthreshold stimulation provided is sufficient to stimulate angiogenesis in the targeted body tissue. The present generator is also capable of checking the lead continuity at a predesignated time. In other preferred embodiments, electrodes and leads can be used with the subthreshold pulse generator. In a preferred embodiment, the electrodes are configured in a manner consisting of bipolar or multiple electrode configurations.

The electrodes are made of conductive metals or organic polymers, or combinations of the two. For example, they can be made of platinium, gold, zirconium, iridium, titanium, certain carbons, stainless steel, silver, copper, tin, nickel, iron, or lithium, or various mixtures, alloys, or amalgams thereof. Design of the electrodes can take on a number of different shapes and sizes, depending on the nature of the target tissue. In the case of heart muscle or other muscle tissues, the electrodes can consist of a straight pin, screw, patch, or the like, which can further comprise various barbs, hooks, or alternate structures for affixing the electrode.

As yet another embodiment, various types of electrical leads similar to those exemplified herein or commonly used with other implantable pulse generators can be used to connect to the power source.

A number of suitable electrodes can function to provide the electrical stimulation. In one feature, the electrode is a surface coil electrode, or heart wire. The surface electrode may be constructed of a platinum alloy or other biocompatible metals. The electrode can be a coil, a cylinder, a wire, or any other shape.

Electrode placement can be done in one of two ways: In the preferred embodiment, electrodes are advanced to the vicinity of the tissue of the heart where the angiogenesis is desired, using the venous system, and left in place. Alternatively, it is possible to place the electrodes in place using minimally invasive surgical procedures, which would allow access to locations that are beyond the reach of the catheters in the vasculature. In either case, bipolar or unipolar stimulation can be applied to generate the electrical fields in the tissue to trigger the electrically responsive promoter. Bipolar stimulation is the preferred method.

The placement of the electrodes would be determined primarily by the method used to implant the electrodes. If the electrodes are placed via a transvenous route then the electrodes should be placed as close as possible to the implanted cells, ischemic tissue, or target area for angiogenesis, understanding that patient anatomy may not allow close proximity of the electrodes. If a non-transvenous implant technique is used, then the stimulating electrodes can usually be placed very close to the ischemic area.

Subthreshold Stimulation of Patients and Cells

The subthreshold stimulation provided is sufficient to stimulate angiogenesis in the targeted body tissue of a patient. As one embodiment, the pulse generator is used to modulate transcription of angiogenic growth factors by the delivery of subthreshold electrical fields.

The invention also provides a subthreshold pulse generator for a patient in need of subthreshold stimulation therapy. In one embodiment, the invention includes a method for reducing or repairing tissue injury by providing a means for regulating angiogenic growth factor production. In one aspect the pulse generator is effective in delivering subthreshold pulses that mediate the repair of injured muscle tissue, such as where ischemic injury has occurred. The method may be applied to damaged cardiac or peripheral muscle tissue by providing a therapeutic stimulus to the surrounding cardiac or muscle tissue or cells. In an alternative embodiment, vascular muscle tissue is stimulated using the subthreshold pulse generator. Subthreshold stimulation of vascular tissue includes stimulation of arteries and veins in a patient.

In one feature of the invention, the present system can be used to treat peripheral arterial occlusive disease (PAOD) or coronary arterial disease (CAD) or stroke, by delivery of a therapeutically effective amount of subthreshold stimulation. It is envisioned that treatment of peripheral arterial occlusive disease (PAOD) or coronary arterial disease (CAD) is achieved by stimulation of angiogenic proteins, such as VEGF and FGF, to enhance blood vessel formation (angiogenesis).

The present invention also provides a novel method of stimulating cells for controlled expression of angiogenic factors. In one preferred embodiment the stimulated cells are muscle cells. In another preferred embodiment the cells are muscle cells, and more preferably, heart, smooth, or skeletal muscle cells. As a preferred embodiment, subthreshold pulses are proved to enhance the cellular production of endogenous angiogenic growth factors of the transplanted cells. In an alternative embodiment, the present device can be used in vitro to pre-stimulate cells which may then be transplanted to the heart. In this process, cells in culture are stimulated in a subthreshold field and used for transplantation. In this process cells may be taken from the patient (autologous cell transplantation) or used from a different patient of the same species (allogenic cell transplantation) or from a different species (xenogenic cell transplantation).

Transplanted cells or grafts may be derived from auto-, allo- or xeno-graphic sources. Transplanted or grafted cells for heart tissue used with pre- or post subthreshold stimulation can be chosen from the group consisting of adult cardiomyocytes, pediatric cardiomyocytes, fetal cardiomyocytes, adult fibroblasts, fetal fibroblasts, adult smooth muscle cells, fetal smooth muscle cells, endothelial cells, and skeletal myoblasts (see U.S. Pat. No. 6,099,832 and procedures described herein for isolation of various cell types). A number of additional procedures are known and described in the art for isolating various primary cell types.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the invention.

Materials and Assays

Human VEGF in samples was quantified using the Human VEGF Immunoassay by Quantikine®. The protocol followed was essentially as described in the Quantikine® Catalog (Number DVE00). The Human VEGF Immunoassay employs a sandwich enzyme immunoassay technique. A monoclonal antibody specific for VEGF is pre-coated on micro-titer plates. Standards and samples are pipetted into wells and any VEGF present is bound by the immobilized antibody. After washing away any unbound substances, an enzyme-linked polyclonal antibody specific for VEGF is added to the wells. Following a wash to remove any unbound antibody-enzyme reagent, a substrate solution is added to the wells and color develops in proportion to the amount of VEGF bound in the initial step. The color development is stopped and the intensity of the color is measured.

Example 1

Sterile 6 well culture plates (Corning) were seeded with cells on six well culture inserts using SmGM growth media; $C_2C_{12}$ cells (mouse myoblasts) were seeded at $7.5 \times 10^3/cm^2$; Human Coronary Smooth Muscle Cells (HCASMC) were seeded at $2.5 \times 10^3/cm^2$. After two days' growth (confluent), the wells were washed twice with electrical stimulation medium (DMEM with 1% bovine serum albumin). 2.0 ml of serum free medium was added but without any fetal bovine serum in the medium. Wells contained approximately 4 ml of total growth medium, approximately 2.0 ml inside well insert and 2.0 ml outside well insert. The cells were electrically stimulated using a circular graphite electrode for 8 hours per stimulation condition. Cells were stimulated at one volt in the stimulation chamber for 1 msec stimulation pulse width with a 4 msec discharge pulse width. The escape period was adjusted to achieve the desired frequency. Samples were harvested after 22 hours post-stimulation. Cell culture supernatants were removed from the well. Any debris or floating cells were removed by centrifuging the supernatants at 300 RPM for 5 minutes prior to freezing the samples at −85° C. A cell count was done on all wells of the culture plate.

Frozen supernatants were thawed and quantified for the amount of VEGF in the samples using the Quantikine Human VEGF Immunoassay. The results (Table 1) indicated that subthreshold stimulation increased the amount of VEGF found in the samples.

TABLE 1

| Cells (seeding density) | Control (pg/$10^3$ cells) | 24 Hz (pg/$10^3$ cells) | 50 Hz (pg/$10^3$ cells) |
|---|---|---|---|
| $C_2C_{12}$ | 0 | .104 | .0556 |
| HCASMC | | | |
| (2 × $10^4$) | 0.410 | 0.360 | 0.670 |
| (4 × 104) | 1.920 | 1.920 | 3.140 |

Example 2

In vivo Subthreshold Stimulation in Canine Model of Regional Ischemic Cardiomyopathy Dogs were initially anesthetized with intramuscular morphine sulfate (4 mg/kg)/ A bolus injection of pentothal (20 mg/kg) was given followed by continuous inhaling of isoflurane (0.5%–2% in oxygen) after endotracheal intubation. A left lateral thoracotomy was performed, and the pericardium opened. A micromanometer pressure transducer (MPC-500, Millar Instruments, Houston, Tex.) was inserted into the left ventricle through an apical incision. Pairs of 5 MHz ultrasonic crystals also was implanted in the area supplied by the distal left anterior descending (LAD) and left circumflex (LCX) arteries just distal to the first diagonal branch of measurement of coronary flow. Two heart wire electrodes were inserted in the LAD perfusion area. A catheter was inserted into the left atrium for injection of colored 15 um microspheres to measure regional myocardial blood flow. Ameriod constrictors were placed on the LAD artery proximal to the flow probe. All wires and tubing were tunneled subcutaneously and brought out through the skin of the dorsal neck. The thoracotomy incision was closed in layers, and a regimen of broad spectrum antibiotics and analgesia was initiated throughout the reperfusion period.

The basic chronology of the experimental protocol after surgery was divided into three periods. The first period (recovery period) occurred in the first week after surgery. After surgery to instrument the dogs, the dogs were allowed to recover. During week one, microspheres were injected for evaluating resting coronary blood flow (CBF) at one week. The second period occurred during weeks 2 through 5 after surgery, and included weekly monitoring of regional stroke work, CBF (LAD and LCX), and left ventricular pressure (LVP) in addition to microsphere injections for evaluating resting CBF. The third period, week 5 through 6 the stimulation occurred for 5 days.

During the six week period, all hemodynamic signals were recorded using an analog-digital converter with sampling at 250 Hz. Regional blood flow was assessed using colored microspheres (15 uM) to quantify the blood flow in the epi- and endomyocardium at the end of the recovery phase (first period), following development of ischemia (second period), and following field stimulation (third period). Tissue and reference blood samples were analyzed in a Spectra Max 250 Microplate Reader Spectrophotometer. Myocardial blood flow was calculated in the subepicardial and subendocardial region of nonischemic and ischemic zones. The potential loss of microspheres from chronic postischemic tissue is corrected by using a rate factor of baseline flow in nonischemic tissue applied to ischemic tissue blood flow data (e,g, ischemic/nonischemic flow).

At the start of week 6 subthreshold pulsing was delivered to the heart using a subthreshold stimulator operated at 50 Hz, 0.1V, with 0.3 ms pulses. The subthreshold stimulator had an operational range of 0 to 1.5 V output in steps of 0.1 V for all 16 allowed settings, pulse widths of 0.1, 0.3, 1.0, and 3.0 m by a series of 4 slide switches. As a result of this pulse output flexibility, the stimulator also had the ability to determine pacing threshold and thus the margin or extent to which the 0.1V, 50 Hz pulses are subthreshold. This is done by setting the device to an assessment mode of 1–3 Hz while stepping up the amplitude to look for VOO pacing capture. Stimulation was delivered via a set of myocardial pacing wires or "Heart-Wires" that were connected to the stimulator through a set of unipolar IS-1 leads to a biopolar IS-1 connector. In addition, the pulse generator contains a combination battery level OK and pacing wire continuity OK indicator with a visible LED light.

Figure 7:
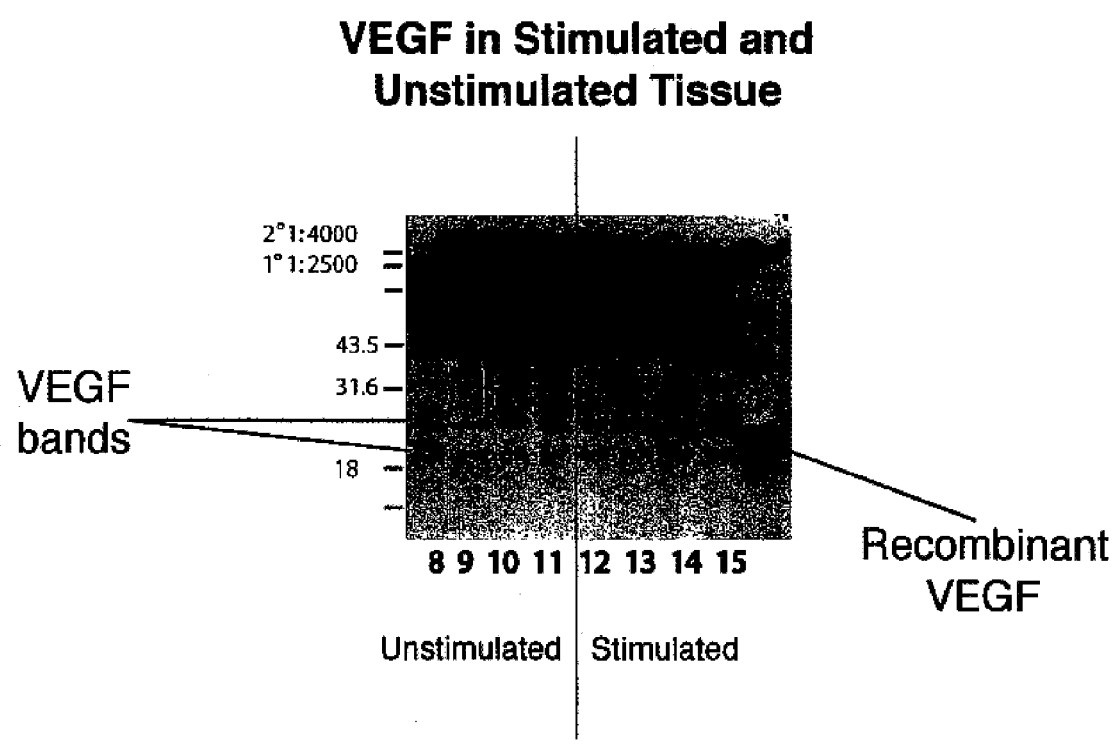
FIG. 7: VEGF Production in Stimulated and Unstimulated Tissue.

The LAD heart area was stimulated for 5 days during week six before terminating the experiment. Sample heart tissue was collected from both stimulated and unstimulated dogs. Heart tissue samples were taken and prepared for Western blot analysis using a VEGF antibody (FIG. 7). Total protein was extracted from postexperimental cardiac tissue. 100 ug of protein was loaded onto each lane of a SDS-Page gel, and run for 15 minutes at 200 Volts. The lanes were exposed to a polyclonal antibody for human VEGF (Santa Cruz). This antibody was blocked by a molecule that blocks the antibody's binding epitope (data not shown), and hence is specific for the VEGF site. Lane 8–11=control group. Lane 8 (nonischemic transmural); Lane 9 (ischemic subepicardium); Lane 10 (ischemic subendocardium); Lane (right ventricle); Lanes 12–15 are treatment (field stimulation) group: Lane 12 (transmural nonischemic); Lane 13 (ischemic subepicardium); Lane 14 (ischemic subendocardium); Lane 15 (right ventricle). Bands for VEGF appear at approximately 26 kD molecular weight. Two bands appear, typical of the two fragments seen for VEGF. Notice that bands consistent with VEGF appear only in Lanes 12–15, i.e. in the treated group. Gels were processed on the same day to avoid variability.

What is claimed is:

1. A subthreshold pulse generator comprising:
   (a) a power supply; and
   (b) a control mechanism interconnected with the power supply to deliver a subthreshold pulse to a targeted cell or tissue;
   wherein the amplitude of the delivered electrical pulse from the power supply has a variable electrical field of about 1 V/cm to about 0.1 V/cm.

2. A subthreshold pulse generator of claim 1, wherein the control mechanism has at least one additional set of components selected from a stimulus timer, output amplitude control, charge balanced pulse timer, stimulation threshold monitor, and a lead continuity monitor.

3. A subthreshold pulse generator of claim 1 wherein the generator has a constant voltage source.

4. A subthreshold pulse generator of claim 1 wherein the amplitude of the delivery of the electrical pulse from the power supply has a variable electrical field of about 1 V/cm.

5. A subthreshold pulse generator of claim 1 wherein the amplitude of the delivery of the electrical pulse from the power supply provides an electrical field of about 0.5 V/cm.

6. A subthreshold pulse generator of claim 1 wherein the amplitude of the delivery of the electrical field from the power supply is about 0.1 V/cm.

7. A subthreshold pulse generator of any one of claims 4, 5, or 6 wherein the variable electrical field is ± about 30%.

8. A subthreshold pulse generator of any one of claims 4, 5, or 7 wherein the variable electrical field is ± about 20%.

9. A subthreshold pulse generator of any one of claims 4, 5, or 7 wherein the variable electrical field is ± about 10%.

10. A subthreshold pulse generator of any one of claims 4, 5, or 7 wherein the variable electrical field is ± about 5%.

11. A subthreshold pulse generator of claim 1 wherein the stimulation period of the electrical pulse from the power supply is less than about 20 msec.

12. A subthreshold pulse generator of claim 1 wherein the stimulation period of the electrical pulse from the power supply is less than about 10 msec.

13. A subthreshold pulse generator of claim 1 wherein the stimulation period of the electrical pulse from the power supply is less than about 5 msec.

14. A subthreshold pulse generator of claim 1 wherein the stimulation period of the electrical pulse from the power supply is less than about 1 msec.

15. A subthreshold pulse generator of claim 1 wherein the stimulation period of the electrical pulse from the power supply is less than about 0.3 msec.

16. A subthreshold pulse generator of claim 1 wherein the frequency of stimulation is about 10 Hz.

17. A subthreshold pulse generator of claim 1 wherein the frequency of stimulation is about 25 Hz.

18. A subthreshold pulse generator of claim 1 wherein the frequency of stimulation is about 40 Hz.

19. A subthreshold pulse generator of claim 1 wherein the frequency of stimulation is about 50 Hz.

20. A subthreshold pulse generator of claim 1 wherein the frequency of stimulation is about 70 Hz.

21. A subthreshold pulse generator of claim 1 wherein the frequency of stimulation is about 85 Hz.

22. A subthreshold pulse generator of claim 1 wherein the frequency of stimulation is about 100 Hz.

23. A subthreshold pulse generator of claim 1, further comprising a plurality of electrodes for delivery of said subthreshold pulse to the targeted cells or tissue.

24. A subthreshold pulse generator of claim 1, wherein at least one electrode is capable of being placed on a catheter and delivered to a target organ transluminally.

25. A subthreshold pulse generator of claim 1, wherein the subthreshold pulse generator provides stimulation to the cells or tissue when the electrodes are in contact with or in proximity of the targeted cells or tissue.

26. A subthreshold pulse generator of claim 1, wherein the amplitude and duration period of the delivery is sufficient to stimulate angiogensis.

27. A subthreshold pulse generator of claim 1, wherein the delivered subthreshold pulse is charge balanced.

28. A subthreshold pulse generator of claim 1, additionally comprising a computer processing unit in electronic communication with the power supply, the computer being programmable to cause the subthreshold pulse generator to deliver a predetermined amount of electrical current or voltage over a predetermined period of delivery to said targeted cells or tissue.

29. A subthreshold pulse generator of claim 1, wherein the electrical pulse generator is implanted in the body.

30. A subthreshold pulse generator of claim 1, wherein the electrical pulse generator is external to the body.

31. A subthreshold pulse generator of claim 1, for delivering an electrical field over a predetermined period of time to a targeted tissue or cell to stimulate the production of VEGF expression.

32. A subthreshold pulse generator of claim 1, wherein the electrical pulse generator is externally controlled.

33. A therapeutic delivery system comprising a subthreshold pulse generator of claim 1, operably linked with mammalian cells or tissue.

34. A therapeutic delivery system of claim 33 wherein the subthreshold pulse generator provides a subthreshold stimulation.

35. A therapeutic delivery system of claim 33 further comprising a plurality of electrodes wherein the subthreshold pulse generator provides stimulation to the cells or tissue from a plurality of electrodes.

36. A therapeutic delivery system of claim 33 wherein the electrical pulse generator provides stimulation to the cell or tissue when the electrodes are in contact with or in proximity of the targeted cells or tissue.

37. A therapeutic delivery system of one of claims 33–36 wherein the stimulated tissue is muscle tissue.

38. A therapeutic delivery system of one of claims 33–36 wherein the stimulated tissue is heart muscle tissue.

39. A therapeutic delivery system of one of claims 33–36 wherein the stimulated tissue is skeletal muscle tissue.

40. A therapeutic delivery system of one of claims 33–36 wherein the stimulated cells are smooth muscle cells.

41. A therapeutic delivery system one of claims 33–36 wherein the stimulated cells are vascular muscle cells.

42. A therapeutic delivery system of one of claims 33–36 wherein the stimulated cells are vascular endothelial cells.

43. A therapeutic delivery system of claim 36 wherein the electrodes are configured in a manner selected from the group consisting of unipolar, bipolar, and multiple electrode configurations.

44. A therapeutic delivery system of claim 33 wherein the electrical pulse generator is implanted.

45. A therapeutic delivery system of claim 33 wherein the electrical pulse generator is external.

46. A therapeutic delivery system of claim 33 wherein the electrical pulse generator is externally controlled.

47. A therapeutic delivery system of claim 33 additionally comprising a sensing electrode for optionally readjusting or synchronizing the period of delivery of the subthreshold pulses.

48. A therapeutic delivery system of claim 33 for delivering an electrical field over a predetermined period of time to targeted cells or tissue to stimulate the production of VEGF expression.

49. A method of treating a patient comprising providing the patient with a subthreshold pulse generator operably linked with targeted mammalian cells or tissues; wherein the subthreshold pulse generator comprises
   (a) a power supply; and
   (b) a control mechanism interconnected with the power supply to deliver a subthreshold pulse to a targeted cell or tissue
   wherein further the amplitude of the delivered electrical pulse from the power supply has a variable electrical field of about 1 V/cm to about 0.1 V/cm.

50. A method of treating a patient comprising providing the patient with a subthreshold pulse generator operably linked to the tissue for acute subthreshold stimulation therapy to improve angiogenesis; wherein the subthreshold pulse generator comprises
   (a) a power supply; and
   (b) a control mechanism interconnected with the power supply to deliver a subthreshold pulse to a targeted cell or tissue
wherein further the amplitude of the delivered electrical pulse from the power supply has a variable electrical field of about 1 V/cm to about 0.1 V/cm.

51. A method of treating a patient comprising using the pulse generator of claim 1, delivering an electrical field over a predetermined period of time to a targeted cells or tissue to stimulate the production of VEGF expression.

52. A method of increasing vascularization in a target tissue comprising providing subthreshold stimulatory pulses to the targeted muscle tissue using the pulse generator; wherein the subthreshold pulse generator comprises
   (a) a power supply; and
   (b) a control mechanism interconnected with the power supply to deliver a subthreshold pulse to a targeted cell or tissue
wherein further the amplitude of the delivered electrical pulse from the power supply has a variable electrical field of about 1 V/cm to about 0.1 V/cm.

53. A method of increasing vascularization in a target tissue wherein the subthreshold stimulatory pulses are targeted to vascular muscle tissue using the pulse generator; wherein the subthreshold pulse generator comprises
   (a) a power supply; and
   (b) a control mechanism interconnected with the power supply to deliver a subthreshold pulse to a targeted cell or tissue
wherein further the amplitude of the delivered electrical pulse from the power supply has a variable electrical field of about 1 V/cm to about 0.1 V/cm.

54. A method of increasing vascularization in a target tissue wherein the subthreshold stimulatory pulses are targeted to heart muscle tissue using the pulse generator; wherein the subthreshold pulse generator comprises
   (a) a power supply; and
   (b) a control mechanism interconnected with the power supply to deliver a subthreshold pulse to a targeted cell or tissue wherein further the amplitude of the delivered electrical pulse from the power supply has a variable electrical field of about 1 V/cm to about 0.1 V/cm.

55. A method of increasing vascularization in a target tissue wherein the subthreshold stimulatory pulses are targeted to skeletal muscle tissue using the pulse generator; wherein the subthreshold pulse generator comprises
   (a) a power supply; and
   (b) a control mechanism interconnected with the power supply to deliver a subthreshold pulse to a targeted cell or tissue wherein further the amplitude of the delivered electrical pulse from the power supply has a variable electrical field of about 1 V/cm to about 0.1 V/cm.

56. A method of treating a patient comprising providing the patient with a subthreshold pulse generator operably linked to a muscle tissue for subthreshold stimulation therapy using the pulse generator; wherein the subthreshold pulse generator comprises
   (a) a power supply; and
   (b) a control mechanism interconnected with the power supply to deliver a subthreshold pulse to a targeted cell or tissue wherein further the amplitude of the delivered electrical pulse from the power supply has a variable electrical field of about 1 V/cm to about 0.1 V/cm.

57. A method of treating a patient of claim 56 wherein stimulated tissue is muscle tissue.

58. A method of treating a patient of claim 56 wherein stimulated tissue is heart muscle tissue.

59. A method of treating a patient of claim 56 where in stimulated tissue is skeletal muscle tissue.

60. A method of treating a patient of claim 56 where in stimulated cells are muscle cells.

61. A method of treating a patient of claim 56 where in stimulated cells are heart muscle cells.

62. A method of treating a patient of claim 56 where in stimulated cells are skeletal muscle cells.

63. A method of treating a patient of claim 56 where in stimulated cells are vascular muscle cells.

64. A method of treating a patient of claim 56 where in stimulated cells are vascular endothelial cells.

65. A method of improving vascularization in a targeted tissue comprising the steps of:
   a. stimulating cultured cells with a subthreshold electrical field using the pulse generator; wherein the pulse generator comprises
      (a) a power supply; and
      (b) a control mechanism interconnected with the power supply to deliver a variable electric field of about 1 V/cm to about 0.1 V/cm; and then subsequently
   b. injecting the stimulated cells into the targeted body tissue.

66. A method of improving vascularization in a target tissue of claim 65 wherein the method additionally comprises further stimulating the injected cells.

67. A method of improving vascularization in a targeted tissue comprising the steps of:
   a. injecting cells into a targeted body tissue; and
   b. stimulating the injected cell area with subthreshold stimulation using the pulse generator wherein the pulse generator comprises:
      (a) a power supply; and
      (b) a control mechanism interconnected with the power supply to deliver a variable electric field of about 1 V/cm to about 0.1 V/cm.

* * * * *